United States Patent
Grodzki et al.

(10) Patent No.: US 11,051,763 B2
(45) Date of Patent: Jul. 6, 2021

(54) METHOD AND APPARATUS FOR DETERMINING A FEATURE CHARACTERIZING INTENTIONAL BREATH-HOLDING BY A PATIENT IN A MEDICAL IMAGING DEVICE

(71) Applicant: Siemens Healthcare GmbH, Erlangen (DE)

(72) Inventors: David Grodzki, Erlangen (DE); Hans Weber, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 35 days.

(21) Appl. No.: 16/438,901

(22) Filed: Jun. 12, 2019

(65) Prior Publication Data

US 2019/0374168 A1    Dec. 12, 2019

(30) Foreign Application Priority Data

Jun. 12, 2018   (DE) .......................... 102018209359.8

(51) Int. Cl.
  *A61B 5/00*  (2006.01)
  *G01R 33/56*  (2006.01)
  *G01R 33/567*  (2006.01)
  *G01R 33/54*  (2006.01)
  (Continued)

(52) U.S. Cl.
  CPC .......... *A61B 5/7267* (2013.01); *A61B 5/0205* (2013.01); *A61B 5/721* (2013.01);
  (Continued)

(58) Field of Classification Search
  CPC ..... A61B 5/7267; A61B 5/0205; A61B 5/721; A61B 5/055; A61B 5/0816; A61B 5/1102;
  (Continued)

(56) References Cited

U.S. PATENT DOCUMENTS 7,276,031 B2 * 10/2007 Norman ................. A61B 5/087
                                                                 600/529
2003/0188757 A1    10/2003 Yanof
(Continued)

FOREIGN PATENT DOCUMENTS

DE    102014219495 A1    4/2015
DE    102014207124 A1    10/2015
(Continued)

OTHER PUBLICATIONS

Wikipedia: "Künstliche Intelligenz" / Wikipedia: "Artificial intelligence".

*Primary Examiner* — Gregory H Curran
(74) *Attorney, Agent, or Firm* — Schiff Hardin LLP (57) ABSTRACT

In a method and medical imaging apparatus for determining a feature characterizing intentional breath-holding by an examination object for acquiring medical raw data with breath-holding algorithm, an algorithm, the algorithm being designed to allocate at least one feature characterizing intentional breath-holding to at least one physiological property. The algorithm includes or accesses trained artificial neural network. A physiological property of the examination object is detected during free breathing of the examination object. The feature characterizing intentional breath-holding by the examination object is determined by the computer, by executing the algorithm with the detected physiological property of the examination object, as an input to the algorithm.

20 Claims, 3 Drawing Sheets

(51) Int. Cl.
*G01R 33/28* (2006.01)
*A61B 5/0205* (2006.01)
*A61B 5/113* (2006.01)
*A61B 5/024* (2006.01)
*A61B 5/055* (2006.01)
*A61B 5/08* (2006.01)
*A61B 5/11* (2006.01)

(52) U.S. Cl.
CPC ......... *G01R 33/283* (2013.01); *G01R 33/543* (2013.01); *G01R 33/5608* (2013.01); *G01R 33/5673* (2013.01); *A61B 5/024* (2013.01); *A61B 5/055* (2013.01); *A61B 5/0816* (2013.01); *A61B 5/1102* (2013.01); *A61B 5/113* (2013.01); *A61B 2576/00* (2013.01)

(58) Field of Classification Search
CPC ... A61B 5/113; A61B 2576/00; G01R 33/283; G01R 33/543; G01R 33/5608; G01R 33/5673
See application file for complete search history.

(56) References Cited

U.S. PATENT DOCUMENTS

| | | |
|---|---|---|
| 2015/0094597 A1 | 4/2015 | Mestha et al. |
| 2015/0293201 A1 | 10/2015 | Assmann et al. |
| 2015/0320342 A1 | 11/2015 | Biber et al. |
| 2015/0335268 A1 | 11/2015 | Biber et al. |
| 2016/0245888 A1 | 8/2016 | Bollenbeck et al. |
| 2016/0313429 A1 | 10/2016 | Van Den Brink et al. |
| 2019/0076098 A1* | 3/2019 | Li .................. A61B 5/7203 |
| 2020/0230439 A1* | 7/2020 | Liu .................. A61B 5/0036 |

FOREIGN PATENT DOCUMENTS

| | | |
|---|---|---|
| DE | 102014208537 A1 | 11/2015 |
| DE | 102014209488 A1 | 11/2015 |
| DE | 102015203385 A1 | 8/2016 |
| EP | 3438688 A1 | 2/2019 |
| WO | WO 03084405 A2 | 10/2003 |
| WO | WO 2015092062 A1 | 6/2015 |

* cited by examiner

METHOD AND APPARATUS FOR DETERMINING A FEATURE CHARACTERIZING INTENTIONAL BREATH-HOLDING BY A PATIENT IN A MEDICAL IMAGING DEVICE

BACKGROUND OF THE INVENTION

Field of the Invention

The present invention concerns a method, a physiological control computer, a medical imaging device, and an electronically readable data carrier for determining a feature characterizing intentional breath-holding by a patient situated in a medical imaging device.

Description of the Prior Art

In a magnetic resonance device (scanner), the body of an examination object to be examined, in particular of a patient, is conventionally exposed to a relatively high static magnetic field, for example of 1.5 or 3 tesla, produced by a magnet of the scanner. In addition, gradient pulses are activated by a gradient coil unit. Radio-frequency pulses (RF pulses), for example excitation pulses, are then emitted by a radio-frequency antenna from suitable antenna devices, causing nuclear spins of particular atoms to be resonantly excited by these RF pulses and being tilted by a defined flip angle with respect to the magnetic field lines of the static magnetic field. Upon relaxation of the excited nuclear spins, RF signals, known as magnetic resonance signals, are emitted, which are received by a reception unit having more RF coil. In this way, medical raw data are acquired, which can be reconstructed to form the desired image data.

Improved techniques for acquiring magnetic resonance signals enable acquisition of time-resolved medical raw data. A movement of the examination object during acquisition typically adversely affects the raw data and the image data to be reconstructed therefrom. In particular, the movement due to breathing of the examination object can be avoided if the medical raw data are acquired while the examination object holds his or her breath.

DE102014207124 A1 describes a device for detecting a movement of a patient by the use of radar. DE102014209488 A1 describes a method for measuring respiration of an examination object on the basis of reflection properties of a coil element arranged beneath the examination object. DE102014208537 A1 describes a device for detecting a movement of a patient by the use of a radio-frequency antenna unit of a magnetic resonance scanner.

SUMMARY OF THE INVENTION

An object of the invention is to provide a particularly simple and accurate method for characterizing intentional breath-holding by an examination object.

The inventive method for determining a feature characterizing intentional breath-holding by an examination object for acquiring medical raw data with breath-holding includes the following method steps.

An algorithm is provided to a computer, the algorithm being designed to allocate at least one feature characterizing intentional breath-holding to at least one physiological property using trained artificial neural network.

A physiological property of the examination object is determined during free breathing of the examination object.

The feature characterizing intentional breath-holding by the examination object based is detected by executing the algorithm with the detected physiological property of the examination object being used as an input to the algorithm.

An interruption in breathing initiated by the examination object can be referred to as intentional breath-holding. In particular, intentional breath-holding can be specified by a start signal. The start signal can be acoustic and/or optical and indicate an instant after which the examination object should interrupt his or her breathing. The examination object is typically a patient. According to the inventive method, medical raw data are acquired from the examination object with breath-holding.

The medical raw data are the data with the medical imaging device. The medical raw data are typically physical signals, which are processed during the course of a reconstruction to form image data. In particular, breathing of the examination object affects the acquisition of the medical raw data.

The algorithm is typically supplied as a program and/or data file. Preferably, this can be accessed within the scope of the inventive method. The algorithm includes a trained artificial neural network, which the algorithm can use and/or which the algorithm can access. Preferably the artificial neural network is used in the course of a Deep-Learning method. The algorithm is designed to produce a correlation between at least one physiological property and at least one feature characterizing intentional breath-holding. The algorithm is preferably configured such that, on the basis of at least one physiological property, a feature characterizing intentional breath-holding can be determined.

The physiological property is preferably detected in a time-resolved manner and/or before the beginning of acquisition of medical raw data. The physiological property can be detected, for example, during positioning and/or following the conclusion of positioning of the examination object relative to the medical imaging device, for example on a couch, which can be used for the acquisition of the medical raw data. Detection of the physiological property with free breathing means that the examination object exhibits normal and/or unchanged breathing behavior during this detection. In particular, no special requirements with respect to breathing are imposed on or given to the examination object for the purpose of this detection.

One feature characterizing intentional breath-holding by an examination object can be, for example, a duration of the interruption in breathing, in particular the maximum tolerable duration for the examination object and/or a proportion, for example 80%, of the maximum tolerable duration. One feature characterizing intentional breath-holding by an examination object can also be a movement of the examination object despite an interruption in breathing, for example due to heartbeat. One feature characterizing intentional breath-holding by an examination object can also be a change over time in the duration of the interruption in breathing and/or a change over time in the movement of the examination object despite an interruption in breathing during the course of several cycles of intentional breath-holding. The feature characterizing intentional breath-holding can in particular be patient-specific and/or dependent on a particular day.

The feature characterizing intentional breath-holding by an examination object is determined by taking into account the algorithm and in particular by taking into account the trained artificial neural network and the at least one detected physiological property of the examination object. The algorithm is preferably configured to characterize the breathing of the examination object, in particular a capacity and/or ability of the examination object to interrupt their breathing, on the basis of the detected physiological property. The algorithm is preferably designed to allocate to the detected physiological property a feature characterizing intentional breath-holding. The algorithm is preferably configured to identify the type of detected physiological property. The detected physiological property typically comprises a quantitative measured value dependent on the type of detected physiological property. When determining the feature, the algorithm and/or the trained artificial neural network typically takes into account the type of detected physiological property and the corresponding quantitative measured value. When determining the feature, the algorithm and/or the trained artificial neural network can also take into account specific data of the examination object, such as, for example its gender, age and/or height.

N advantage of the inventive method is that an anticipated ability of the examination object, for example to interrupt his or her breathing, can be determined on the basis of the patient's normal breathing. For example, at least one sensor for determining the breathing movement of the examination object can be used here during the course of detection of the physiological property. According to the inventive method, the characterization of an intentional interruption in breathing can occur at the same time as a required preparation of acquisition of the medical raw data.

In particular, the inventive method makes a dedicated experimental, patient-specific determination of an ability to breath-hold unnecessary. Requesting the examination object to try holding their breath and thereby, for example, explicitly measuring the maximum duration of an interruption in breathing of the examination object in this situation, is omitted. A measurement of this kind does not ensure reproducibility of the interruption in breathing, whereas the inventive method can take this into account. The examination object is spared the task of such a measurement of breath-holding before acquisition of the medical raw data. In particular, the number of cycles for interrupting the breathing of the examination object can be reduced. As a result, the examination object can hold his or her breath better during the acquisition of the medical raw data. This improves the quality of the medical raw data and/or shortens the duration of acquisition of the medical raw data. The acquisition of medical raw data with breath-holding is more comfortable for the examination object as a result. No break is required between such a measurement of breath-holding before acquisition of the medical raw data and acquisition of the medical raw data, and this shortens the duration of the examination.

Similarly, the medical personnel are alleviated from having to estimate intentional breath-holding by the examination object. The work flow thus is also simplified for the medical staff. Intentional breath-holding by the examination object can be characterized more precisely. This can prevent the situation where the examination object may hold his or her breath for a longer time than assumed, whereby the duration of acquisition of medical image data with breath-holding would be unnecessarily prolonged. The inventive method also prevents the situation where the examination object may hold his or her breath for a shorter time than assumed, whereby the quality of the medical raw data would be impaired.

Access to the trained artificial neural network enables this kind of determination even without knowledge and/or supplying of a function and/or dependency between the detected physiological property and the feature to be determined with simultaneously particularly accurate characterization of intentional breath-holding.

In an embodiment of the method, the physiological property of the examination object is acquired by the medical imaging device that subsequently acquires the medical raw data from the examination object, in particular a magnetic resonance scanner. As a physiological property, for example a movement of the examination object can accordingly be detected as described in DE 10 2015 203 385 A1. An advantage of this embodiment is that, when using a magnetic resonance scanner, the magnetic resonance scanner itself has the components required for detection of the movement. The movement, in particular a regular and/or cyclical movement due to breathing and/or heartbeat can be detected particularly accurately using known navigator data sets or by other techniques. According to this embodiment, the physiological property is detected preferably as soon as the examination object is positioned inside the patient-receiving region of the scanner. Typically, there is a break between the time of positioning of the examination object and the start of acquisition of the medical raw data, in which break the medical staff selects and/or parameterizes the MR control sequences. This break can be used in a time-efficient manner for acquisition of the at least one physiological property. In addition to this embodiment of the method, the physiological property can be acquired optically and/or on the basis of sensors.

In an embodiment of the method, the physiological property of the examination object is detected optically by a sensor. For example, movement of the examination object, typically due to breathing and/or heartbeat, can be detected by a camera. Optical monitoring of the movement of the examination object can take place two-dimensionally and/or three-dimensionally. In addition and/or alternatively, a sensor can detect a movement of the examination object for example by radar signals and/or acceleration measurement. The sensor can also be designed to detect a physiological property acoustically, such as noise due to breathing and/or a heartbeat. The sensor can be at least partially positioned on the examination object. The sensor can be integrated in the medical imaging device, in particular in a housing that surrounds the medical imaging device. An advantage of this embodiment is in that a movement and/or other physiological property of the examination object can be acquired particularly accurately and conveniently. Different types of physiological properties, such as a periodicity, a time characteristic and/or an intensity due to breathing and/or a heartbeat, can be detected. This is made possible by this embodiment.

In an embodiment of the method, the physiological property includes at least one of the following types:
time characteristic of breathing and/or a heartbeat
periodicity of breathing and/or a heartbeat
movement due to breathing and/or a heartbeat
noise due to breathing and/or a heartbeat
intensity of a movement due to breathing and/or a heartbeat
type of breathing.

A physiological property is typically characterized by the type and its quantity and/or its size. The algorithm is designed to take into account the type and the quantity of the physiological property during allocation. A noise due to breathing can result for example due to the bronchial tubes. The type of breathing is preferably based on the free breathing of the examination object and/or takes into account the positioning of the examination object, which it has during acquisition of the medical raw data. The type of breathing preferably comprises abdominal breathing and/or diaphragmatic breathing and/or chest breathing. Typically, different physiological properties are detected using different sensors. When determining the feature characterizing intentional breath-holding by the examination object, preferably at least two types of a physiological property are considered. The algorithm and/or the trained artificial neural network is/are preferably designed for an allocation between a feature characterizing intentional breath-holding by the examination object and at least two types of a physiological property. Intentional breath-holding can be characterized particularly accurately and reproducibly as a result.

In an embodiment of the method, a further method step, acquisition of medical raw data with breath-holding is planned, by taking into account the determined feature characterizing intentional breath-holding by the examination object. In particular, the acquisition of medical raw data by a magnetic resonance scanner typically takes longer than the examination object can hold his or her breath. MR control sequences can be divided in the course of planning of the acquisition into sub-sections, wherein the duration of a sub-section is selected to correspond to a maximum and/or comfortable duration of the interruption in breathing determined for the examination object. Planning can include an optimization of a subsequent acquisition of medical raw data in respect of duration of the acquisition and/or quality of the medical raw data. As a result, the acquisition of medical raw data can be matched particularly individually with the examination object and/or the requirements of the medical staff.

In another embodiment of the method, an additional method step, medical raw data are acquired by the medical imaging scanner with breath-holding by taking into account the determined feature characterizing intentional breath-holding by the examination object. Acquisition is preferably planned before acquisition of the medical raw data by taking into account the determined feature. The duration of acquisition can be shortened and/or the quality of the acquired medical raw data can be improved as a result. Consequently, acquisition of medical raw data can be matched particularly individually with the examination object and/or the requirements of the medical staff.

In another embodiment of the method, provides while acquiring the medical raw data, the actual breathing of the examination object is monitored and acquisition of outstanding medical raw data can be adapted to the actual breathing. In particular, the breathing of the examination object and/or a feature characterizing this can be checked by monitoring the breath-holding actually performed. Monitoring typically occurs during acquisition of the medical raw data. If the breath-holding actually performed differs from the feature determined by means of the inventive method, then parts of the acquisition of the medical raw data, which are outstanding up to the determination of the deviation, are adapted to the breath-holding actually performed. The adjustment to the breath-holding actually performed can include a division of the acquisition into sub-sections, with the duration of a sub-section being selected to correspond with an actual duration of an interruption in breathing. As a result, the acquisition can be individually adapted to potentially changed breathing of the examination object and/or the quality of the acquired medical raw data can be improved.

In another embodiment of the method, while acquiring the medical raw data, the actual breathing of the examination object is monitored and the trained artificial neural network is updated on the basis of the actual breathing. Updating of the trained artificial neural network brings about continuous training of the trained artificial neural network. As a result, the trained artificial neural network can be continuously expanded and improved by Deep-Learning methods. Similarly, for example an input (confirmation) by the medical staff as to the correctness of the determined feature can be taken into account during updating. As a result, the trained artificial neural network, and the algorithm, is continuously improved.

In an embodiment of the method, the trained artificial neural network is of a type generated according to the following method steps.

A database containing a number of data entries is provided to a computer, each data entry being allocated to at least one feature characterizing intentional breath-holding and at least one physiological property.

An artificial neural network is also provided to the computer. The computer trains the artificial neural network using the allocation determined by the data entries, so the trained artificial neural network enables an allocation of a physiological property to a feature characterizing intentional breath-holding.

The database is preferably generated on the basis of a large number of test persons. Generation of a data entry of the database preferably comprises detection of at least one physiological property with free breathing and a breath-holding test of a test person. With a breath-holding test, preferably the maximum tolerable duration and/or a proportion, for example 80%, of the maximum tolerable duration of an intentional interruption in breathing is determined. An artificial neural network trained in this way is particularly robust and allows reliable characterization of intentional breath-holding by an examination object.

Furthermore, the invention encompasses a physiological control computer that is in communication with a physiological property detector, and that includes a determining processor. The physiological control computer is configured to implement the method for determining a feature characterizing intentional breath-holding by an examination object for acquisition of medical raw data with breath-holding as described above. The detector detects a physiological property of the examination object with free breathing of the examination object. The determining processor is designed to determine the feature characterizing intentional breath-holding by the examination object, on the basis of the detected physiological property of the examination object and on the basis of an algorithm. The algorithm involves a trained artificial neural network and is designed to allocate at least one feature characterizing intentional breath-holding to at least one physiological property. The determining processor is designed to execute the algorithm.

For this purpose, the determining processor has an input, a processor core, and an output. The determining processor can be supplied with the algorithm and/or the detected physiological property via the input. Further functions, algorithms or parameters required in the method also can be supplied to the determining processor via the input. The feature, determined by the determining processor, characterizing intentional breath-holding by the examination object and/or further results of an embodiment of the inventive method are supplied via the output. The determining processor and/or the detector can be integrated in the medical imaging scanner. The determining processor and/or the detector can also be installed separately from the medical imaging scanner. The determining processor and/or the detector can be connected to the medical imaging scanner.

The determining processor can be connected to a memory and/or include a memory, in which algorithm is stored, which is designed to allocate at least one feature characterizing intentional breath-holding to at least one physiological property, and which involves a trained artificial neural network.

Furthermore, the invention encompasses a medical imaging apparatus having a data acquisition scanner and an inventive physiological control computer. The inventive medical imaging apparatus is configured to carry out the method according to the invention for determining a feature characterizing intentional breath-holding by an examination object and for acquisition of medical raw data with breath-holding by taking into account the feature characterizing intentional breath-holding.

Embodiments of the inventive medical imaging apparatus and/or the inventive physiological control computer are designed analogously to the embodiments of the inventive method. The medical imaging apparatus and/or the physiological control computer can have further control components, which are necessary and/or advantageous for carrying out the inventive method. The medical imaging apparatus and/or the physiological control computer can also be designed to send control signals and/or to receive and/or process control signals in order to carry out the inventive method. The physiological control computer is preferably part of the control computer of the inventive medical imaging apparatus. Computer programs and further software can be stored on a memory of the physiological control computer, by which the processor of the physiological control computer automatically controls and/or carries out a process sequence of the inventive method.

The present invention also encompasses a non-transitory, computer-readable data storage medium encoded with programming instructions (program code) that, when loaded into a computer or computer system that operates a magnetic resonance apparatus cause the computer or computer system to implement any or all embodiments of the method according to the invention, as described above.

Examples of electronically readable data carriers are a DVD, a magnetic tape or a USB stick, on which electronically readable control information, in particular software, is stored.

The advantages of the inventive physiological control computer, the inventive medical imaging apparatus, and the inventive electronically readable data carrier essentially correspond to the advantages of the inventive method for determining a feature characterizing intentional breath-holding, which have been described above in detail. Features, advantages or alternative embodiments mentioned in this connection can likewise also be transferred to the other aspects of the invention.

DESCRIPTION OF THE PREFERRED EMBODIMENTS

Figure 1:
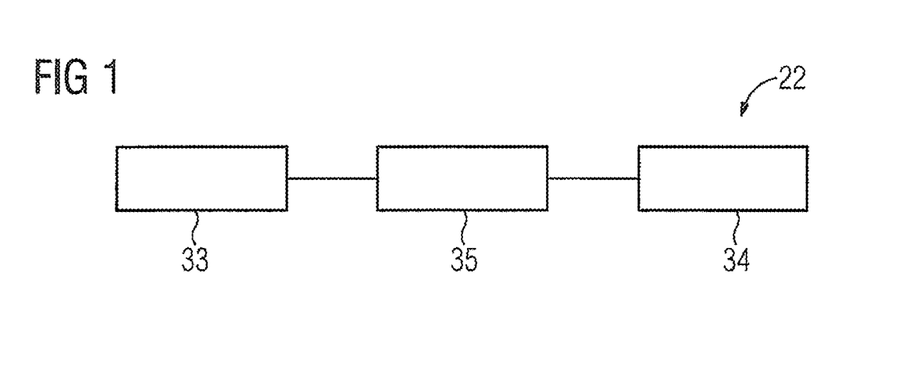
FIG. 1 is a block diagram of an inventive physiological control computer.

FIG. 1 shows a physiological control computer 22 that includes a memory 33, a physiological property detector 34 and a determining processor 35. Preferably, an algorithm is stored on the memory 33 and/or on the determining processor 35, which algorithm is designed to allocate at least one feature characterizing intentional breath-holding to at least one physiological property, and which comprises a trained artificial neural network. The physiological property detector 34 is designed to detect a physiological property of the examination object with free breathing of the examination object. The determining processor 35 is designed to determine the feature characterizing intentional breath-holding by the examination object on the basis of the algorithm and the detected physiological property of the examination object. The memory 33, the detector 34 and the determining processor 35 can be connected together and/or be at least partially integrated in each other. In particular, the determining processor 35 can include the memory 33. The detector 34 can be designed, for example, as a camera or as a movement sensor or as an acceleration sensor. Further embodiments of the detector 34 are possible. The control computer 22 is accordingly configured for implementing the inventive method for determining a feature characterizing intentional breath-holding by an examination object for acquisition of medical raw data with breath-holding.

Figure 2:
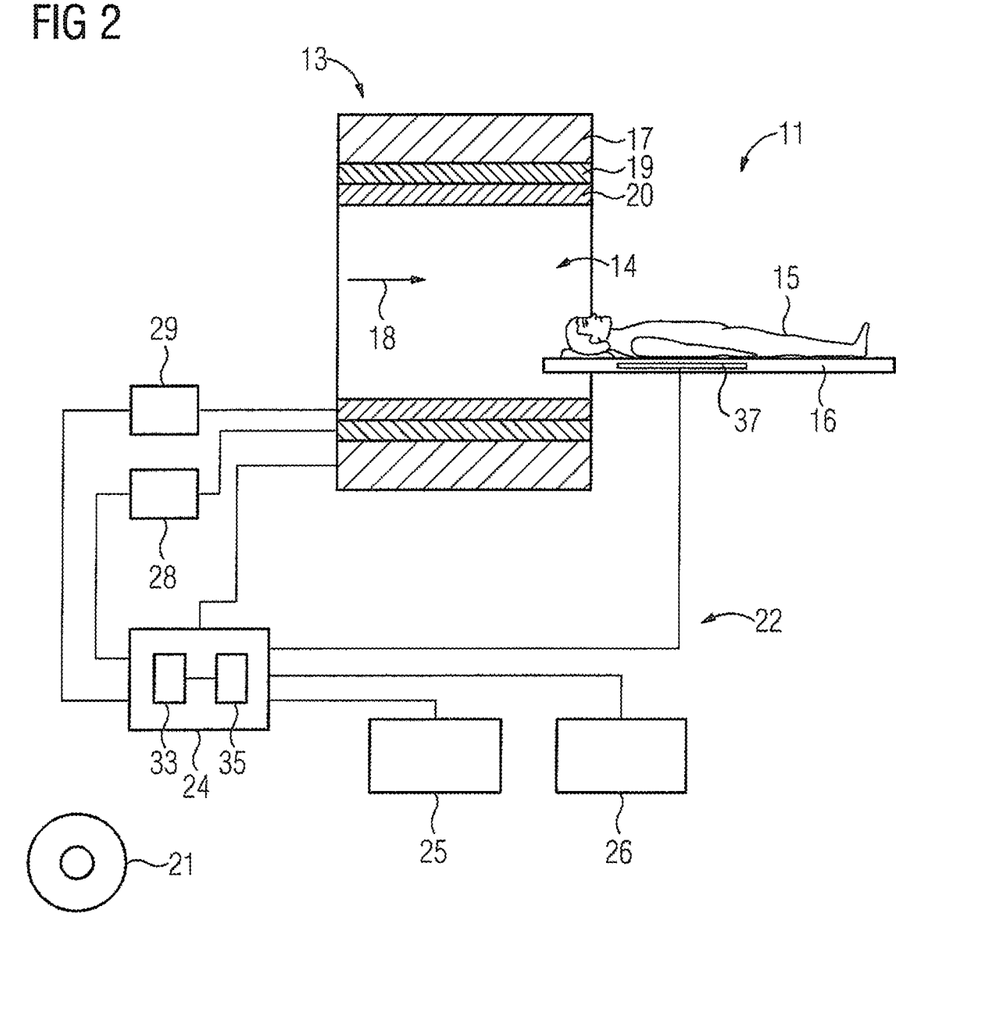
FIG. 2 schematically illustrates a first embodiment of an inventive medical imaging apparatus.

FIG. 2 shows a magnetic resonance apparatus 11 as an example of a first embodiment of an inventive medical imaging device for carrying out the inventive method, in a schematic diagram. The design of the medical imaging device is not limited to a magnetic resonance apparatus 11, but can also be formed by other medical imaging devices that are considered expedient to those skilled in the art, such as computer tomography devices, PET devices, ultrasound devices, etc.

The magnetic resonance apparatus 11 has a data acquisition scanner 13 having a basic field magnet 17 that generates a strong and constant basic magnetic field 18. The magnetic resonance scanner 13 has a cylindrical patient-receiving region 14 for receiving an examination object 15, with the patient-receiving region 14 being cylindrically surrounded at its circumference by the basic field magnet 17. The examination object 15 can be moved by a patient-positioning device 16 of the scanner 13 into the patient-receiving region 14. The patient-positioning device 16 for this purpose has a patient bed arranged so as to move inside the scanner 13.

The scanner 13 also has a gradient coil unit 19 for spatial encoding during imaging. The gradient coil unit 19 is controlled by a gradient controller 28. The scanner 13 also has a radio-frequency (RF) antenna unit 20, which in the illustrated case is designed as a body coil permanently integrated in the scanner 13, and a radio-frequency antenna controller 29. The radio-frequency antenna unit 20 is controlled by the radio-frequency antenna controller 29 so as to irradiate radio-frequency pulses into an examination space that is essentially formed by the patient-receiving region 14. The radio-frequency pulses give certain nuclear spins in the examination object 15 a magnetization that causes those excited nuclear spins to be deflected from the direction of the basic magnetic field 18. As those excited nuclear spins relax, they emit radio-frequency signals, called magnetic resonance signals, which are detected as raw data, and which are processed in a known manner so as to produce image data of the examination object 15.

For controlling the basic field magnet 17, the gradient controller 28 and the radio-frequency antenna controller 29, the magnetic resonance apparatus 11 has a control computer 24. The control computer 24 centrally controls the magnetic resonance apparatus 11, in order to execute MR control sequences. Furthermore, the control computer 24 includes a reconstruction processor (not shown) for reconstruction of medical image data from the raw data acquired during the magnetic resonance scan. The magnetic resonance apparatus 11 has a display unit 25. Control information, such as control parameters and reconstructed image data, can be displayed on the display unit 25, for example on at least one monitor, for the operator. Furthermore, the magnetic resonance apparatus 11 has an input unit 26 via which the operator can enter information and/or control parameters during a scanning process. The control computer 24 can include the gradient controller 28 and/or the radio-frequency antenna controller 29 and/or the display unit 25 and/or the input unit 26.

The magnetic resonance apparatus 11 also has a physiological control computer 22 in communication with a sensor 37 that serves as the physiological property detector 34. The physiological control computer 22 includes and a determining processor 35. The physiological control computer 22 and the determining processor 35 thereof are configured to carry out the inventive method for determining a feature characterizing intentional breath-holding by an examination object for acquisition of medical raw data with breath-holding.

For this purpose, the physiological control computer 22, in particular the determining processor 35 thereof, has computer programs and/or software, which can be loaded directly into a storage device of the physiological control computer 22, in order to provide program code that causes the inventive method for determining a feature characterizing intentional breath-holding by the examination object 15 to be executed in the determining processor 35. The determining processor 35 has for this purpose a core processor (not separately shown), which is configured to execute the computer programs and/or software. The computer programs and/or software can be stored on an electronically readable data carrier 21 designed separately from the control computer 24 and/or determining processor 35, which can be loaded into the physiological control computer 24. The determining processor 35 can be integrated in the control computer 24. The memory 33 can be integrated in the control computer 24 and/or in the determining processor 35. The determining processor 35 can be integrated in the control computer 24. The memory 33, the control computer 24 and/or the determining processor 35 can be connected together. The memory 33, the control computer 24 and/or the determining processor 35 can be designed at least partially separate from each other. In this first embodiment of the inventive medical imaging device the detector 34 is a sensor 37 integrated in the patient-positioning device 16, so as to detect movement of the examination object 15. The sensor 37 can also be of the type that detects an alternative and/or further physiological property of the examination object. The sensor 37 can operate, for example, based on electromagnetic interaction with the examination object 15 and/or based on sound and/or based on acceleration.

In addition or as an alternative to the sensor 37, the radio-frequency antenna unit 20 and/or the radio-frequency antenna controller 29 can serve as the physiological property detector 34. In addition to the resonant radio-frequency pulses necessary for the generation of magnetic resonance signals, the radio-frequency antenna unit 20 and/or the radio-frequency antenna controller 29 can be designed to emit further radio-frequency pulses, and acquire further MR data (navigator data), from movement of the examination object 15 can be ascertained.

The illustrated magnetic resonance apparatus 11 can of course have further conventional components. The general mode of operation of magnetic resonance apparatuses is known to those skilled in the art, so a more detailed description is not necessary herein. The magnetic resonance apparatus 11, together with the physiological control computer 22, and the detector 34 is therefore configured to carry out an inventive method.

A method for determining a feature characterizing intentional breath-holding by an examination object 15 can also be in the form of a computer program product, which implements the method on the physiological control computer 22 when it is executed on the physiological control computer 22. Similarly, an electronically readable data carrier 21 with electronically readable control information (code) stored thereon can be present, which causes the described method to be executed when the data carrier 21 is loaded into the physiological control computer 22.

Figure 3:
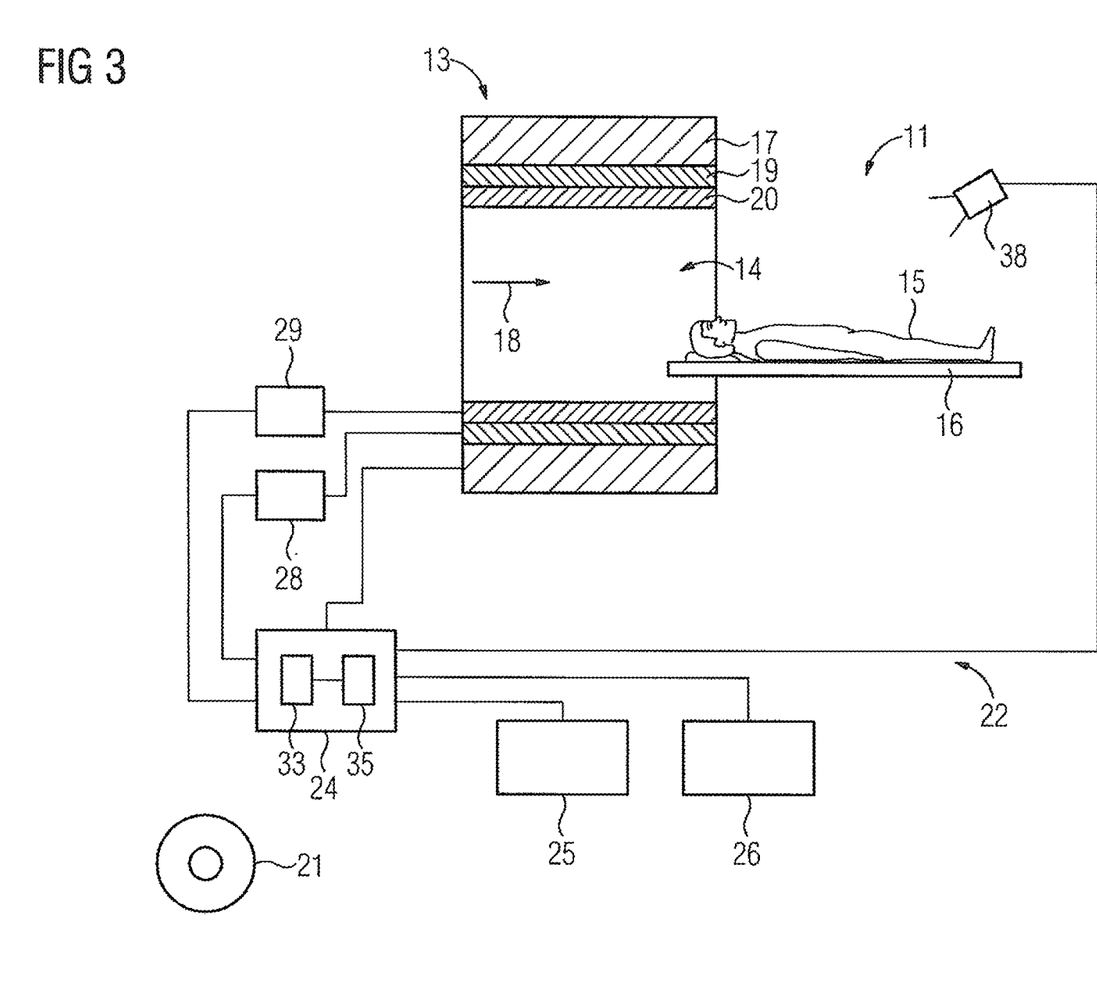
FIG. 3 schematically illustrates a second embodiment of an inventive medical imaging device apparatus.

FIG. 3 shows a magnetic resonance apparatus 11 as an example of a second embodiment of an inventive medical imaging device 12 for carrying out the inventive method, in a schematic diagram. The second embodiment of the inventive medical imaging device differs from the first embodiment illustrated in FIG. 2 in the design of the physiological property detector 34. In the embodiment of FIG. 3, the detector 34 is designed as a camera 38 for optical detection of the physiological property of the examination object 15. The camera 38 is designed to detect a movement on the basis of heartbeat and/or breathing of the examination object 15. In addition and/or as an alternative to the camera 38, the radio-frequency antenna unit 20 and/or the radio-frequency antenna controller 29 can serve as the detector 34.

Figure 4:
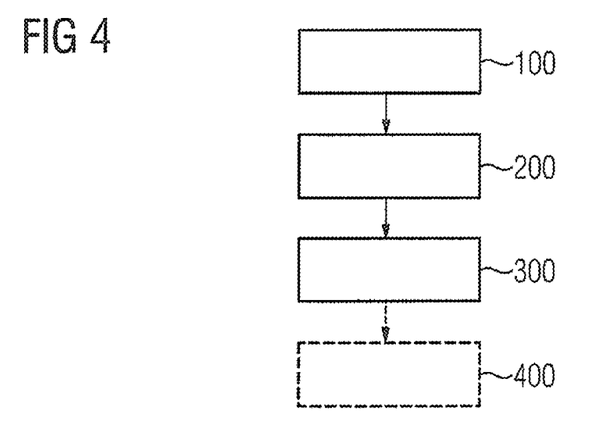
FIG. 4 is a flowchart of a first embodiment of the inventive method.

FIG. 4 shows a flowchart of a first embodiment of the inventive method for determining a feature characterizing intentional breath-holding by the examination object 15 for acquisition of medical raw data with breath-holding.

The method begins with method step 100, supplying an algorithm, which is deigned to allocate at least one feature characterizing intentional breath-holding to at least one physiological property, and which comprises a trained artificial neural network. Method step 200 is the detection of a physiological property of the examination object 15 with free breathing of the examination object 15. Here, free breathing can be detected even before the beginning of acquisition of medical raw data by means of the physiological property detector 34. A physiological property of the examination object 15 can be detected by the medical imaging apparatus 11 being configured for acquisition of navigator data of the examination object 15 and/or optically by the camera 38 and/or on the basis of sensors such as sensor 34. In method step 300 the feature characterizing intentional breath-holding by the examination object 15 is determined on the basis of the algorithm and the detected physiological property of the examination object. A further optional method step 400 can include planning acquisition of medical raw data with breath-holding by taking into account the determined feature characterizing intentional breath-holding by the examination object 15.

The physiological property can be at least one of the following properties:
    time characteristic of breathing and/or a heartbeat
    periodicity of breathing and/or a heartbeat
    movement due to breathing and/or a heartbeat
    noise due to breathing and/or a heartbeat intensity of a movement due to breathing and/or a heartbeat type of breathing.

Figure 5:
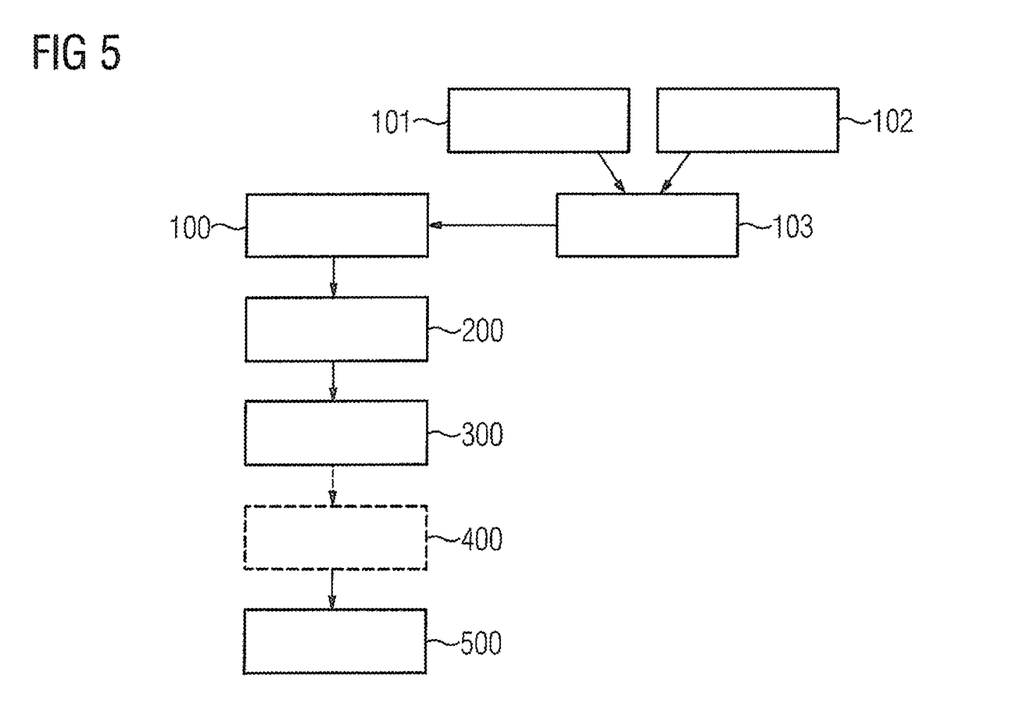
FIG. 5 is a flowchart of a second embodiment of the inventive method.

FIG. 5 shows a flowchart of a second embodiment of an inventive method for determining a feature characterizing intentional breath-holding by an examination object 15 for acquisition of medical raw data with breath-holding. The second embodiment differs from first embodiment by a method step 500 using the determined feature, and optional method steps 101, 102, 103 determining the trained artificial neural network in more detail. The first embodiment can be expanded by the method steps 400 and/or 500 and/or 101, 102, 103 independently of each other.

The trained artificial neural network can have been generated according to the method steps 101, 102, 103. Method step 101 is supplying a database having a number of data entries, which are each allocated at least one feature characterizing intentional breath-holding and at least one physiological property. Method step 102 is supplying an artificial neural network. Method step 103 provides training of the artificial neural network using the allocation determined by the data entries, with the artificial neural network enabling allocation of a physiological property to a feature characterizing intentional breath-holding.

In the additional method step 500, medical raw data are acquired by the medical imaging apparatus 12 from the examination object 15 with breath-holding by taking into account the determined feature. The actual breathing of the examination object 15 can be monitored and acquisition of outstanding medical raw data adapted to the actual breathing. Alternatively and/or additionally, the trained artificial neural network can also be updated on the basis of the actual breathing.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for determining a feature characterizing intentional breath-holding by an examination object for acquiring medical raw data with breath-holding, said method comprising:
   providing an algorithm to a computer, said algorithm allocating at least one feature characterizing intentional breath-holding to at least one physiological property, using a trained artificial neural network, wherein the algorithm is generated on the basis of a plurality of test examination objects;
   detecting said at least one physiological property of the examination object during free breathing of the examination object; and
   determining the feature characterizing intentional breath-holding by the examination object in said computer by executing the algorithm with the detected physiological property of the examination object as an input to said algorithm.

2. The method as claimed in claim 1, comprising detecting the physiological property of the examination object is detected by operation of a medical imaging device configured to acquire said medical raw data of the examination object.

3. The method as claimed in claim 1 wherein said medical imaging device is a magnetic resonance apparatus, and detecting said physiological property of the examination object by operating the magnetic resonance apparatus in order to acquire navigator data from the examination object, and determining said physiological property of the examination object from said navigator data.

4. The method as claimed in claim 1, comprising detecting the physiological property of the examination object is detected optically.

5. The method as claimed in claim 1, comprising detecting the physiological property of the examination object is detected using at least one sensor.

6. The method as claimed in claim 1, comprising detecting the physiological property as at least one of:
   a time characteristic of breathing and/or a heartbeat of the examination object,
   a periodicity of breathing and/or a heartbeat of the examination object,
   movement due to breathing and/or a heartbeat of the examination object,
   noise due to breathing and/or a heartbeat of the examination object,
   intensity of a movement due to breathing and/or a heartbeat of the examination object,
   type of breathing of the examination object.

7. The method as claimed in claim 1, comprising in said computer planning acquisition of said medical raw data with breath-holding, taking into account the determined feature characterizing intentional breath-holding by the examination object.

8. The method as claimed in claim 1, comprising producing the trained artificial neural network by:
   supplying said training computer a database comprising a plurality of data entries, each data entry being allocated to at least one feature characterizing intentional breath-holding and at least one physiological property;
   supplying said artificial neural network to said training computer;
   training the artificial neural network in said training computer using the allocation determined by the data entries, so as to produce the artificial neural network that enables an allocation of a physiological property to a feature characterizing intentional breath-holding.

9. The method as claimed in claim 8 wherein said training computer is said computer that executes said algorithm.

10. The method as claimed claim 1 comprising acquiring said medical raw data by operation of a medical imaging device with breath-holding by taking into account the determined feature characterizing intentional breath-holding by the examination object.

11. The method as claimed in claim 10, comprising, while acquiring the medical raw data, monitoring actual breathing of the examination object and adapting the acquisition of said medical raw data to the actual breathing.

12. The method as claimed in claim 10, comprising, while acquiring the medical raw data, monitoring actual breathing of the examination object and updating the trained artificial neural network based on the actual breathing.

13. The method as claimed in claim 1, wherein the at least one feature characterizing intentional breath-holding comprises a change over time in a duration of an interruption in breathing.

14. The method as claimed in claim 1, wherein the at least one feature characterizing intentional breath-holding comprises a change over time in a movement of the examination object despite an interruption in breathing during a course of several cycles of intentional breath-holding.

15. A physiological control system for determining a feature characterizing intentional breath-holding by an examination object for acquiring medical raw data with breath-holding, comprising:

a computer provided with an algorithm, said algorithm allocating at least one feature characterizing intentional breath-holding to at least one physiological property, using trained artificial neural network, wherein the algorithm is generated on the basis of a plurality of test examination objects;

a detector that detects said at least one physiological property of the examination object during free breathing of the examination object; and said computer being configured to determine the feature characterizing intentional breath-holding by the examination object in said computer by executing the algorithm with the detected physiological property of the examination object as an input to said algorithm.

16. A medical imaging device for determining a feature characterizing intentional breath-holding by an examination object for acquiring medical raw data with breath-holding, said medical imaging device comprising:

a computer provided with an algorithm, said algorithm allocating at least one feature characterizing intentional breath-holding to at least one physiological property, using trained artificial neural network, wherein the algorithm is generated on the basis of a plurality of test examination objects;

a detector that detects said at least one physiological property of the examination object during free breathing of the examination object; and said computer being configured to determine the feature characterizing intentional breath-holding by the examination object in said computer by executing the algorithm with the detected physiological property of the examination object as an input to said algorithm.

17. A medical imaging device as claimed in claim 16 wherein said detector is an optical detector that detects said at least one physiological property optically.

18. A medical imaging device as claimed in claim 16 wherein said detector is a sensor.

19. A medical imaging device as claimed in claim 16 wherein said scanner is a magnetic resonance data acquisition scanner, and wherein said magnetic resonance data acquisition scanner serves as said detector and detects navigator data from which said at least one physiological property is determined.

20. A non-transitory, computer-readable data storage medium encoded with programming instructions, said storage medium being loaded into a computer that is in communication with a detector that detects at least one physiological property of an examination object, said programming instructions causing said computer to:

receive an algorithm that allocates at least one feature characterizing intentional breath-holding to at least one physiological property, using trained artificial neural network, wherein the algorithm is generated on the basis of a plurality of test examination objects;

receive said at least one physiological property of the examination object, detected during free breathing of the examination object; and determine the feature characterizing intentional breath-holding by the examination object, by executing the algorithm with the detected physiological property of the examination object as an input to said algorithm.

* * * * *